United States Patent [19]

Jacquet et al.

[11] Patent Number: 4,522,808
[45] Date of Patent: Jun. 11, 1985

[54] ANTI-SUNBURN COMPOSITIONS CONTAINING 2-PHENYL-INDOLE DERIVATIVES

[75] Inventors: Bernard Jacquet, Antony; Gérard Lang, Epinay-sur-Seine; Alain Malaval, Aulnay-sous-Bois, all of France

[73] Assignee: Societe Anonyme dite: L'Oreal, Paris, France

[21] Appl. No.: 428,755

[22] Filed: Sep. 30, 1982

Related U.S. Application Data

[63] Continuation of Ser. No. 178,582, Aug. 15, 1980, abandoned, which is a continuation-in-part of Ser. No. 716,650, Aug. 23, 1976, abandoned.

[51] Int. Cl.³ .................... A61K 7/06; A61K 7/021; A61K 7/42; A61K 9/12
[52] U.S. Cl. .......................................... 424/59; 8/406; 8/407; 252/522 R; 424/DIG. 1; 424/DIG. 5; 424/47; 424/61; 424/63; 424/70; 424/71; 424/72; 424/78; 424/80; 424/81
[58] Field of Search ............................................ 424/59

[56] References Cited

U.S. PATENT DOCUMENTS

| | | | |
|---|---|---|---|
| 2,334,348 | 11/1943 | Miglarese | 424/59 |
| 3,095,422 | 6/1963 | Duennenberger et al. | 424/59 |
| 3,489,768 | 1/1970 | Short et al. | 424/59 |
| 3,491,114 | 1/1970 | Suh | 424/59 |
| 3,726,898 | 4/1973 | Duncan et al. | 424/59 |
| 3,901,899 | 8/1975 | Gassman | 424/59 |
| 3,903,108 | 9/1975 | Krutak | 424/59 |

FOREIGN PATENT DOCUMENTS

| | | | |
|---|---|---|---|
| 435811 | 9/1935 | United Kingdom | 424/59 |

Primary Examiner—Dale R. Ore

Attorney, Agent, or Firm—Cushman, Darby & Cushman

[57] ABSTRACT

Anti-sunburn compositions are provided which comprise, as active ingredient, at least one compound of the general formula:

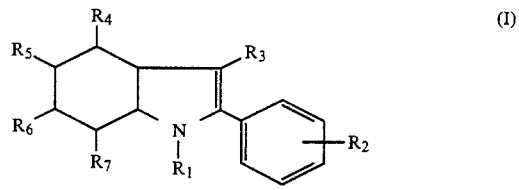

in which:
$R_1$ is selected from hydrogen, alkyl radicals containing 1 to about 12 carbon atoms and optionally branched carboxyalkyl radicals containing 1 to 4 carbon atoms;
$R_2$ is selected from hydrogen, alkoxy radicals containing 1 to 4 carbon atoms, at least one alkyl and carboxyalkyl radical containing 1 to 4 carbon atoms, and halogen atoms.
$R_3$ is selected from hydrogen, carboxyalkyl radicals containing 1 to 4 carbon atoms and $—S—R_8$ radicals, each of $R_4$, $R_5$, $R_6$ and $R_7$ is independently selected from hydrogen, and alkyl, carboxyalkyl and alkoxy radicals containing 1 to 4 carbon atoms, provided that if $R_3$ denotes hydrogen, at least one of the radicals $R_1$ $R_2$, $R_4$, $R_5$, $R_6$ and $R_7$ is not hydrogen, in an amount of at least about 0.05% by weight based on the total weight of the composition. These compounds have good solubility properties enabling a large number of different types of formulation to be prepared, these formulations being adjusted to meet the requirements of the skin to be protected.

4 Claims, No Drawings

ANTI-SUNBURN COMPOSITIONS CONTAINING 2-PHENYL-INDOLE DERIVATIVES

This application is a continuation of application Ser. No. 178,582 filed Aug. 15, 1980, now abandoned, which in turn is a continuation-in-part of application Ser. No. 716,650 filed Aug. 23, 1976, now abandoned.

The present invention relates to anti-sunburn compositions containing certain derivatives of 2-phenylindole.

The use of 2-phenyl-indole as an absorber of ultraviolet radiation in cosmetic compositions is already known from British Specification No. 435,811. However, its solubility in the cosmetic solvents is very low, which considerably restricts its use in this field.

U.S. Pat. Nos. 3,370,063 and 3,491,114, relate to certain derivatives of 5,6-dimethoxy-indole. However, these compounds are not particularly soluble, and they absorb the radiation largely outside the erythematous zone.

It is the object of the invention to provide cosmetic compositions capable not only of retarding the development of solar erythema, without inhibiting the pigmentation of the skin, but also of providing a range of formulations which is extremely varied, in accordance with the protective effect desired and the degree of sensitivity of the type of skin to be protected.

It is well known that the solar radiation reaching the surface of the earth comprises three types of radiation, namely ultraviolet radiation, visible radiation and infra-red radiation.

Certain ultraviolet radiation, that is to say the highest energy radiation, is responsible for solar erythema and can, if exposure is prolonged, cause severe burns and even cutaneous cancers.

In fact, the ultraviolet flux is made up of, firstly, an erythematous flux of wavelengths between 290 and 320 nm (nanometers) which causes the appearance of the erythema which gives way, after a period of 2 to 5 days, to a natural pigmentation due to a photo-induced melanogenesis, and, secondly, a non-erythematous bronzing flux of wavelengths between 320 and 370 nm which causes an immediate pigmentation which appears between 2 and 5 hours after the start of the exposure, this pigmentation being due to a photo-oxidation of certain precursors of melanin present in the skin.

It is thus of value to be able to retard the appearance of the solar erythema and its development into burns, thereby permitting a longer exposure, or more intense exposure as is generally the case in the mountains, whilst preserving to the greatest extent the beneficial effect of natural bronzing.

The present invention provides to an anti-sunburn composition which corresponds to the abovementioned advantages and which contains, as a protective agent against the actinic rays, in a cosmetic vehicle which can form a continuous film which can easily be spread over the epidermis, at least one compound having the general formula:

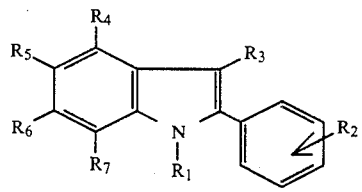

in which:

$R_1$ denotes H, an alkyl radical containing 1 to 12 carbon atoms or an optionally branched carboxyalkyl radical containing 1 to 4 C, e.g. $CH_3$, $C_4H_9$, $C_{12}H_{25}$ or $CH_2COOH$, $R_2$ denotes H, an alkoxy radical containing 1 to 4 carbon atoms, at least one alkyl or carboxyalkyl radical containing 1 to 4 C, or a halogen atom, e.g. Cl, $OCH_3$ or $CH_3$, $R_3$ denotes H, a carboxyalkyl radical containing 1 to 4 C, e.g. $CH_2CH_2COOH$ or $CH_2COOH$, or a $—S—R_8$ radical, in which $R_8$ is an alkyl radical containing 1 to 12 carbon atoms, e.g. $C_{12}H_{25}$, $C_8H_{17}$, $C_4H_9$, or a

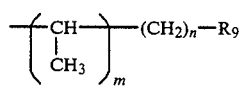

in which
$R_9$ denotes one of the radicals;

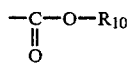

in which $R_{10}$ is H or an alkyl radical containing 1 to 4 carbon atoms, as in $—SCH_2COOC_2H_5$ or

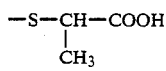

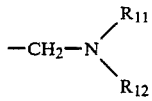

in which $R_{11}$ and $R_{12}$ independently denote H or an alkyl radical containing 1 to 4 carbon atoms, as in $—S(CH_2)_3N(CH_3)_2$, $—S(CH_2)_2N(CH_3)_2$ or $—S(CH_2)_2NHC_4H_9$, or

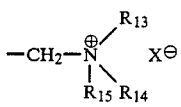

in which $R_{13}$, $R_{14}$ and $R_{15}$ independently denote an alkyl radical containing 1 to 4 carbon atoms and X denotes an anion of an inorganic or organic acid, and m is 0 or 1 and n is 0, 1 or 2, $R_4$, $R_5$, $R_6$ and $R_7$ independently denote H, or a carboxyalkyl, alkyl or alkoxy radical containing 1–4 C, e.g. $CH_3$, $OCH_3$ or $CH_2COOH$, provided that if $R_3$ denotes H, at least one of the radicals $R_1$, $R_2$, $R_4$, $R_5$, $R_6$ and $R_7$ is different from H.

The compounds of the formula (I) exhibit excellent absorption of ultraviolet radiation in the wavelength range from 290 to 320 nm, as is indicated by the rapid reduction in the ratio of (transmitted erythematous flux)/(incident erythematous flux) or % $\phi_E^T$, in accordance with the concentration of the active product as well as with the choice of the solvent and of the ingredients contained in the composition, this rapid reduction ensuring the protection of the skin through the formation of a protective film of a thickness which is generally from 3 to 20 microns. The choice of the compound of the formula (I), of the concentration used and of the cosmetic vehicle furthermore makes it possible to adapt the composition of the invention to the protection of various types of epidermis.

The abovementioned ratio has the advantage of directly showing the degree of protection against erythematous radiation for a given concentration and a given cosmetic solvent or vehicle, as indicated by B. M. CUMPERLIK according to the method described in the publication in J. Soc. Cosmet. Chem. 23, page 333, 1972.

The compounds of the formula (I) furthermore exhibit excellent transmission of ultraviolet radiation in the wavelength range from 320 to 370 nm, which is responsible for non-erythematous bronzing, that is to say the immediate bronzing of the epidermis, which thus contributes to its natural protection. This is shown by the high value of the ratio: (transmitted non-erythematous bronzing flux)/(incident non-erythematous bronzing flux) or $\phi_{BNE}^T$, also determined according to the method mentioned above.

Table I below indicates the value of the ratios $\phi_E^T$ and $\phi_{BNE}^T$, as a percentage of flux transmitted, for a certain number of compounds of the formula (I) and for concentrations of 1 to 4 g per 100 g of solvent; the measurements were carried out on a 10 microns thick film.

TABLE I

| Ex. No. | COMPOUNDS FORMULA | SOL-VENT | % $\phi_E^T$ 10 microns thick film, concentration in g % | | | | % $\phi_{BNE}^T$ 10 microns thick film, concentration in g % | | | |
|---|---|---|---|---|---|---|---|---|---|---|
| | | | 1 | 2 | 3 | 4 | 1 | 2 | 3 | 4 |
| 1 | 4,6-dimethyl-2-phenylindole | A | 8.95 | 0.88 | 0.10 | 0.014 | 49.0 | 39.2 | 35.5 | 33.4 |
| 2 | 4,7-dimethyl-2-phenylindole | A | 9.16 | 0.93 | 0.11 | 0.015 | 46.3 | 33.5 | 28.3 | 25.3 |
| 3 | 4,6-dimethyl-2-phenylindole (isomer) | A | 12.7 | 1.83 | 0.29 | 0.051 | 37.7 | 28.5 | 25.5 | 23.9 |
| 4 | 3-(carboxymethylthio)-2-phenylindole | A | 24.7 | 6.3 | 1.65 | 0.47 | 65.6 | 48.6 | 39.4 | 33.8 |
| 5 | 5-methoxy-3-(carboxymethylthio)-2-(4-chlorophenyl)indole | A | 38 | 14.8 | 5.85 | 2.4 | 54.2 | 35.7 | 27.2 | 22.7 |
| 6 | 5-methoxy-3-(carboxymethylthio)-2-phenylindole | A | 31.85 | 10.4 | 3.8 | 1.2 | 62.2 | 45.8 | 37.7 | 33.2 |

TABLE I-continued

| Ex. No. | COMPOUNDS FORMULA | SOL-VENT | $\phi_E^T$ 10 microns thick film, concentration in g % | | | | $\phi_{BNE}^T$ 10 microns thick film, concentration in g % | | | |
|---|---|---|---|---|---|---|---|---|---|---|
| | | | 1 | 2 | 3 | 4 | 1 | 2 | 3 | 4 |
| 7 | 2-phenyl-3-(S—C$_{12}$H$_{25}$)-indole (NH) | A | 32.8 | 10.9 | 3.7 | 1.3 | 68.7 | 51.6 | 41.65 | 35.4 |
| 8 | 2-phenyl-3-(S(CH$_2$)$_3$—N(CH$_3$)$_2$)-indole (NH) | A | 22.5 | 5.2 | 1.27 | 0.33 | 62.8 | 45.7 | 36.8 | 31.6 |
| 9 | 2-phenyl-3-(S(CH$_2$)$_3$—N$^{\oplus}$(CH$_3$)$_3$)-indole (NH), CH$_3$SO$_4^{\oplus}$ | B | 42.6 | 18.5 | 8.2 | 4.75 | 82.7 | 70.5 | 61.7 | 55.3 |
| 10 | 2-phenyl-3-(S(CH$_2$)$_2$—N(CH$_3$)$_2$)-indole (NH) | A | 23.2 | 5.5 | 1.35 | 0.35 | 60.8 | 42.9 | 33.7 | 28.3 |
| 11 | 2-phenyl-3-(SCH$_2$COOC$_2$H$_5$)-indole (NH) | A | 24.95 | 6.35 | 1.70 | 0.45 | 63.6 | 46.7 | 37.9 | 32.7 |
| 12 | 5-CH$_3$-2-phenyl-3-(SCH$_2$COOC$_2$H$_5$)-indole (NH) | A | 22.85 | 5.4 | 1.35 | 0.40 | 57.7 | 41.2 | 33.5 | 29.1 |
| 13 | 2-phenyl-3-(SCH$_2$COOH)-indole (NCH$_3$) | A | 36.4 | 14.2 | 6.15 | 3.0 | 87.2 | 77.3 | 69.4 | 63.2 |
| 14 | 4,7-(CH$_3$)$_2$-2-phenyl-3-(SCH$_2$COOH)-indole (NH) | A | 29.75 | 9.05 | 2.85 | 1.37 | 69.0 | 51.4 | 40.9 | 34.1 |

TABLE I-continued

| Ex. No. | COMPOUNDS FORMULA | SOL-VENT | $\phi_E^T$ 10 microns thick film, concentration in g % | | | | $\phi_{BNE}^T$ 10 microns thick film, concentration in g % | | | |
|---|---|---|---|---|---|---|---|---|---|---|
| | | | 1 | 2 | 3 | 4 | 1 | 2 | 3 | 4 |
| 15 | [indole with SCH₂COOH at 3-position, phenyl at 2-position, CH₃ at 6 and 7] | A | 28.1 | 8.1 | 2.4 | 0.72 | 58.7 | 40.5 | 31.4 | 26.2 |
| 16 | [indole with SCH₂COOH at 3-position, phenyl at 2-position, CH₃ at 5] | A | 21.3 | 4.7 | 1.1 | 0.27 | 59 | 42.6 | 34.7 | 30.2 |
| 17 | [indole with SCH₂COOH at 3-position, phenyl at 2-position, CH₃ at 5 and 7] | A | 32.5 | 10.65 | 3.6 | 1.25 | 68.1 | 51.3 | 41.8 | 35.9 |
| 18 | [indole with phenyl at 2-position, CH₃ at 6 and 7] | A | 11.18 | 1.40 | 0.195 | 0.03 | 43.6 | 32.9 | 28.8 | 26.3 |
| 19 | [indole with S—C₈H₁₇ at 3-position, phenyl at 2-position] | A | 33.6 | 11.4 | 3.96 | 1.41 | 68.2 | 50.8 | 40.7 | 34.3 |
| 20 | [indole with S—C₄H₉ at 3-position, phenyl at 2-position] | A | 20.3 | 4.3 | 0.95 | 0.23 | 59.2 | 41.4 | 32.4 | 27.2 |
| 21 | [indole with S—CH(CH₃)—CO₂H at 3-position, phenyl at 2-position] | A | 24.8 | 6.3 | 1.65 | 0.46 | 62.9 | 44.9 | 35.1 | 29.2 |
| 22 | [indole with phenyl at 2-position, C₄H₉ on N] | A | 25 | 7.22 | 2.68 | 1.34 | 85.6 | 75.4 | 67.95 | 62.3 |
| 23 | [indole with CH₃O at 5-position, phenyl at 2-position] | A | 14.3 | 2.19 | 0.35 | 0.059 | 39.3 | 29.9 | 26.9 | 25.2 |

TABLE I-continued

| Ex. No. | COMPOUNDS FORMULA | SOL-VENT | $\phi_E^T$ 10 microns thick film, concentration in g % | | | | $\phi_{BNE}^T$ 10 microns thick film, concentration in g % | | | |
|---|---|---|---|---|---|---|---|---|---|---|
| | | | 1 | 2 | 3 | 4 | 1 | 2 | 3 | 4 |
| 24 | 5-CH₃ indole, 2-phenyl (NH) | A | 9.66 | 1.06 | 0.19 | 0.018 | 46.1 | 37.5 | 34.5 | 32.9 |
| 25 | indole, 2-(4-OCH₃-phenyl) (NH) | EtOH | 23.1 | 5.54 | 1.39 | 0.37 | 62.5 | 48.5 | 42.2 | 38.6 |
| 26 | 4,5-di-CH₃ indole, 2-phenyl (NH) | A | 9.16 | 0.94 | 0.108 | 0.014 | 39.2 | 29.2 | 25.6 | 23.4 |
| 27 | indole, 2-phenyl, N-CH₃ | A | 14.45 | 2.88 | 0.99 | 0.52 | 79.0 | 66.9 | 59.3 | 54.1 |
| 28 | indole, 2-phenyl, N-C₁₂H₂₅ | A | 36.2 | 14.1 | 6.2 | 3.2 | 91.3 | 84.4 | 78.9 | 74.5 |
| 29 | 5,6-di-CH₃ indole, 2-phenyl (NH) | A | 13.2 | 2.01 | 0.34 | 0.063 | 38.0 | 29.3 | 26.5 | 24.6 |
| 30 | 5,7-di-CH₃ indole, 2-phenyl, 3-S-CH(CH₃)-CO₂H (NH) | A | 33.0 | 11.05 | 3.77 | 1.32 | 64.7 | 47.2 | 37.7 | 31.9 |
| 31 | 5-CH₃O indole, 2-phenyl, 3-S-(CH₂)₂-NH-C₄H₉ (NH) | A | 7.65 | 0.67 | 0.068 | 0.0077 | 37.7 | 26.4 | 22.0 | 19.3 |

TABLE I-continued

| Ex. No. | COMPOUNDS FORMULA | SOLVENT | $\phi_E^T$ 10 microns thick film, concentration in g % | | | | $\phi_{BNE}^T$ 10 microns thick film, concentration in g % | | | |
|---|---|---|---|---|---|---|---|---|---|---|
| | | | 1 | 2 | 3 | 4 | 1 | 2 | 3 | 4 |
| 32 | indole with S-(CH₂)₃-N(CH₃)₃⁺ I⁻ at 3-position, 2-phenyl, NH | B | 46.8 | 22.2 | 10.7 | 5.3 | 84.5 | 73.1 | 64.43 | 57.8 |
| 33 | 2-phenyl indole, N-CH₂-CO₂H | EtOH | 58.9 | 35.7 | 22.3 | 14.6 | 96.9 | 94.0 | 91.3 | 88.8 |
| 34 | 5,6-dimethoxy-2-phenyl indole | EtOH | 59.5 | 36.01 | 22.06 | 13.6 | 55.9 | 37.3 | 28.9 | 24.9 |
| 35 | 5,6-dimethoxy-3-(S-CH₂-CO₂H)-2-phenyl indole | EtOH | 49.0 | 24.5 | 12.5 | 6.4 | 52.8 | 33.4 | 24.6 | 20.1 |
| 36 | 3-(CH₂-CH₂-CO₂H)-2-phenyl indole | EtOH | 58.6 | 34.5 | 20.5 | 12.2 | 87.05 | 77.3 | 69.9 | 64.1 |
| 37 | 4,7-dimethyl-3-(CH₂-CO₂H)-2-phenyl indole | EtOH | 33.6 | 12.3 | 4.9 | 2.2 | 84.8 | 74.2 | 66.6 | 60.9 |
| 38 | 2-(p-tolyl) indole | EtOH | 23.98 | 6.34 | 2.05 | 0.89 | 82.3 | 72.0 | 65.7 | 61.5 |
| 39 | 3-(S-CH₂-CO₂H)-2-(3,4-dimethylphenyl) indole | EtOH | 26.7 | 7.41 | 2.2 | 0.73 | 73.9 | 60.2 | 52.4 | 47.6 |

TABLE I-continued

| Ex. No. | COMPOUNDS FORMULA | SOL-VENT | $\phi_E^T$ % 10 microns thick film, concentration in g % | | | | $\phi_{BNE}^T$ % 10 microns thick film, concentration in g % | | | |
|---|---|---|---|---|---|---|---|---|---|---|
| | | | 1 | 2 | 3 | 4 | 1 | 2 | 3 | 4 |
| 40 | 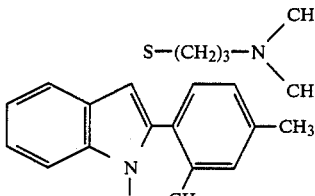 | EtOH | 52.0 | 27.8 | 15.4 | 8.9 | 92.5 | 86.0 | 80.3 | 75.4 |
| 41 | 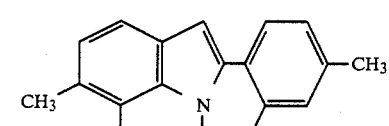 | EtOH | 31.8 | 10.6 | 3.9 | 1.7 | 84.8 | 75.1 | 68.6 | 64.1 |
| 42 | 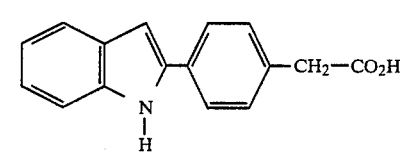 | EtOH | 8.45 | 0.81 | 0.09 | 0.01 | 46.2 | 36.7 | 33.4 | 31.7 |
| 43 | 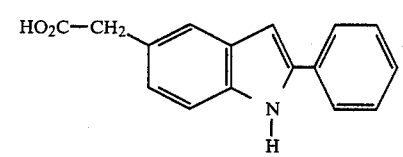 | EtOH | 23.5 | 5.8 | 1.5 | 0.41 | 62.2 | 49.5 | 44.1 | 41.2 |

A = "miglyol" - triglycerides of $C_8$-$C_{12}$ fatty acids of vegetable origin
B = water
EtOH = ethanol As is shown in Table I, the compounds used as UV filters in the compositions of the invention have an excellent % absorption ratio $\phi_E^T$ for the erythematous flux while retaining a very good % transmission ratio $\phi_{BNE}^T$ for the non-erythematous bronzing flux, and they are completely harmless to the skin as well as possessing good chemical and photochemical stability.

Their properties are particularly noteworthy as regards solubility. In fact, almost all the compounds of the formula (I) have a markedly greater solubility in usual cosmetic solvents than that of 2-phenyl-indole, which corresponds to the compound of the formula (I) in which all the radicals $R_1$ to $R_7$ are H.

The filter compounds of the formula (I), while already exhibiting all the properties desired of UV filters, furthermore possesses another very noteworthy and unusual property which is that the compounds can be used at effective concentrations in practically all the usual vehicles for anti-UV cosmetic compositions.

The invention thus essentially resides in the discovery of the advantageous solubility properties of a category of compounds resulting from the introduction, into the 2-phenyl-indole nucleus, of at least one of the radicals as defined in the general formula (I), and in the utilisation of these properties in the preparation of cosmetic compositions, especially anti-sunburn compositions.

Certain compounds of the formula (I) in which $R_3$ denotes the radical

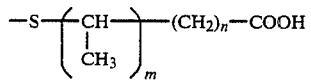

and especially the compounds for which, respectively, m=0 with n=1, or m=1 with n=0, possess, furthermore, an anti-inflammatory activity mentioned in general terms in a publication by J. BOURDAIS and A. LORRE (European Journal of Medicinal Chemistry, 9 (3) page 269, 1974).

These anti-inflammatory properties are particularly effective and valuable in the compositions (for topical applications) of the invention because, in addition to the filtering power already mentioned, they contribute firstly to retarding the appearance of the erythema and secondly to reducing its intensity. As a result, by comparison with the other compounds of the general formula (I) having similar ratios $\phi_E^T$ and $\phi_{BNE}^T$, the compounds for which $R_3$ has the abovementioned meaning exhibit a greater anti-sunburn efficiency when used in the same concentration and with the same vehicle.

The anti-sunburn compositions of the invention can be in a great variety of forms, by appropriate selection of the compound or compounds of the formula (I) with the vehicle used, by varying the radicals $R_1$ to $R_7$ and especially the radicals $R_3$ to $R_7$; the vehicle can in particular be based on water, alcoholic solvents, fatty solvents or their mixtures.

It can be mentioned here that 2-phenyl-indole is insoluble in cold isopropyl myristate whilst the solubility of 5,7-dimethyl-2-phenyl-indole in the same solvent is greater than 5% by weight.

The compositions of the invention can be in the form of a liquid comprising a single phase containing a single solvent or a mixture of solvents such as an oil/alcohol mixture, or can be an oil-in-water or water-in-oil emulsion, a dispersion or a suspension, a homogeneous paste, a semi-solid product or a product containing a propellant, and are thus anti-sunburn cosmetic compositions such as an oil, a lotion, an aerosol (of the oil, foam or "spray" type), a gel, a cream for normal or dry skin, a milk or a lipstick.

The following may be mentioned particularly as constituents which may be present in the compositions: lanoline, vaseline, glycerol, triglycerides of fatty acids, polyethylene glycols, oxyethyleneated fatty alcohols, esters such as isopropyl palmitate, myristate and stearate, oleyl oleate and butyl stearate, animal, vegetable or mineral oils, fatty alcohols, glycerol monostearate, and organic and mineral waxes; these constituents are generally used in an amount of about 1 to 97% by weight. Isopropyl palmitate or isopropyl myristate are particularly suitable for the preparation of compositions which can be applied in the form of a continuous film, of the desired thickness, to the epidermis.

The compounds of the formula (I) are suitably used in the anti-sunburn cosmetic compositions of the invention at a concentration of 0.5 to 10% by weight relative to the weight of the composition and preferably 1 to 6%, the remainder of the composition being made up to 100% by weight, firstly by usual cosmetic ingredients, and secondly by the solvent or mixture of solvents present in the vehicle, especially miglyol.

Amongst the cosmetic ingredients used there may be mentioned thickeners, softeners, superfatting agents, emollients, wetting agents and surface-active agents, as well as preservatives, anti-foam agents, perfumes or any other compatible ingredient usually employed in cosmetics.

Amongst the solvents used there may be mentioned water, lower monoalcohols or polyalcohols as well as their mixtures, or aqueous-alcoholic or oil/alcohol solutions, the alcohols preferably used being ethanol, isopropyl alcohol, propylene glycol, glycerol and sorbitol, and the aqueous-alcoholic mixtures used preferably being mixtures of water and ethyl alcohol.

The abovementioned protective composition can either be colourless or coloured with the dyestuffs and/or pigments usually employed for anti-sunburn compositions and especially iron oxides in proportions of about 0.001% to 0.050% by weight relative to the total weight of the composition.

The invention also relates to a self-protected cosmetic composition, that is to say a composition of which the constituents are protected against light radiation by the presence of a compound of the formula (I) used in an amount of, say, 0.5 to 5% by weight, especially if the composition contains one or more compounds particularly sensitive to ultraviolet rays such as, for example, photosensitive dyestuffs used at a concentration of the order of 0.0005% to 0.05% of the total weight of the composition in question, such as, in particular, the triarylmethane derivatives, such as crystal violet, methyl violet, methyl green or Victoria Blue BSA.

In addition to the photosensitive dyestuff or dyestuffs and the compound of the formula (I) the composition of the invention can in particular contain film-forming agents, cosmetic resins, foaming agents and perfumes, as well as the other abovementioned ingredients.

The following may be mentioned as film-forming agents and cosmetic resins usable in the invention: polyvinylpyrrolidone, vinylpyrrolidone/vinyl acetate copolymers in which the monomer ratios are from 70/30 to 30/70, vinyl acetate/unsaturated carboxylic acid copolymers such as a copolymer containing 90% of vinyl acetate and 10% of crotonic acid, terpolymers of methyl methacrylate/stearyl methacrylate/dimethylaminoethyl methacrylate, completely quaternised with dimethyl sulphate, the monomers being used particularly in the ratio 20/23/57, and a terpolymer of vinyl acetate/allyl stearate/allyloxyacetic acid, especially in the ratio of 80/15/5, maleic anhydride/methyl vinyl ether copolymers such as those commercially referred to as "Gantrez AN" as well as the ethyl, isopropyl and butyl esters of these copolymers, and maleic anhydride/butyl vinyl ether copolymers.

As examples of cosmetic compositions containing a compound of the formula (I) either to protect the photosensitive dyestuffs contained in the composition or to avoid their degradation, there may be mentioned compositions for the hair, such as hair lacquers, plasticising wavesetting lotions, treatment wavesetting lotions or disentangling wavesetting lotions, shampoos, dyeing shampoos, hair dyeing solutions, nail varnishes, treatment creams for the epidermis and foundation creams; these compositions can thus be packaged advantageously in glass bottles or bottles of a transparent plastic, without any risk of deterioration.

In general terms, if the composition of the invention contains a propellant, whether this be an antisunburn composition or a composition containing compounds of the formula (I) intended for the protection of the constituents of the composition itself, a customary propellant is used, such as the propellants based on chlorofluoromethane known by the name of "Freon" and in particular "Freon 12" or dichlorodifluoromethane, as well as an inert gas or a mixture of inert gases.

The invention of course also relates to a process for the protection of cosmetic compositions prone to deteriorate due to light radiation, according to which process at least one compound of the formula (I) is incorporated, in the proportion of 0.05 to 5% by weight, into these solutions.

The invention also relates to the new compounds which correspond to the general formula:

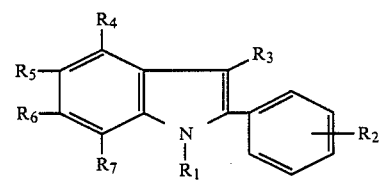

in which:
$R_1$ is selected from a hydrogen atom, alkyl radicals containing 1 to about 12 carbon atoms, and optionally branched carboxy alkyl radicals containing 1 to 4 carbon atoms,
$R_2$ is selected from a hydrogen atom, alkyl, carboxyalkyl and alkoxy radicals containing 1 to 4 carbon atoms and a halogen atom, but $R_2$ cannot be a —CH$_2$COOH in the para position to the indole base, $R_3$ is selected from a hydrogen atom, carboxyalkyl radicals containing 1 to 4 carbon atoms and —S—$R_8$ groups in which:

$R_8$ represents an aliphatic radical contains [1] 2 to about 12 carbon atoms, or represents the group

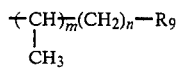

in which
n is 0, 1 or 2 and m is 0 or 1,
$R_9$ is selected from

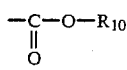

or

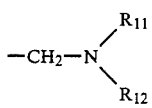

or

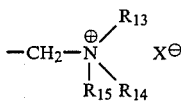

in which each of $R_{10}$, $R_{11}$ and $R_{12}$ is independently selected from a hydrogen atom and aliphatic radicals containing 1 to 4 carbon atoms, each of $R_{13}$, $R_{14}$ and $R_{15}$ is independently selected from aliphatic radicals containing 1 to 4 carbon atoms, and $X^\ominus$ is a halide, alkyl-sulphate, arylsuphonate or methanesulphonate anion, and each of $R_4$, $R_5$, $R_6$ and $R_7$ is independently selected from hydrogen alkyl, alkoxy and carboxyalkyl groups containing 1 to 4 carbon atoms, with the proviso that if $R_3$ denotes hydrogen, at least one of the radicals $R_1, R_2, R_4, R_5, R_6$ and $R_7$ is not hydrogen;

if $R_1, R_2, R_3, R_4, R_5, R_6$ and $R_7$=H, $R_1$ is not $CH_3$ and if $R_1, R_2, R_3, R_4, R_6$ and $R_7$=H, the radical $R_5$ is not $CH_3$ or $CH_3O$.

Preferred compounds are those in which if $R_3$ denotes a hydrogen atom, and $R_1$ and at least one of the substituents $R_4$ to $R_7$ is not hydrogen, $R_1$ and $R_5$ are not methyl simultaneously.

Even more preferable are those compounds wherein $R_9$ is selected from

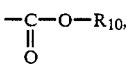

or

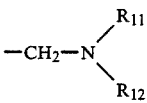

or

-continued

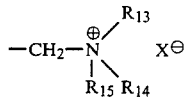

in which $R_{10}$ is an aliphatic radical containing 1 to 4 carbon atoms, each of $R_{11}$, $R_{12}$, $R_{13}$, $R_{14}$ and $R_{15}$ is independently selected from aliphatic radicals containing 1 to 4 carbon atoms, and $X^\ominus$ is a halide, alkyl-sulphate, arylsuphonate or methanosulphonate anion.

Most preferable are those compounds having the above formula but in which (i) if $R_3$ denotes a hydrogen atom, $R_1$ and at least one of the substituents $R_4$ to $R_7$ is not hydrogen and $R_1$ and $R_5$ are not methyl simultaneously, (ii) if $R_3$ denotes

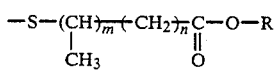

and if m=0 and n=1, at least one of the substituents $R_4$ to $R_7$ is not hydrogen if $R_1$ and $R_{10}$ are both hydrogen, and $R_5$ is not methoxy if $R_2$ denotes hydrogen, whilst if m=1 and n=0, at least one of the substituents $R_1$, $R_2$, $R_4$ to $R_7$ is not hydrogen if $R_{10}$ denotes hydrogen, and (iii) if $R_3$ denotes

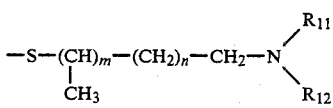

and if m=0 and n=1, and $R_{11}$ and $R_{12}$ denote methyl and $R_1$ and $R_4$ to $R_7$ denote hydrogen, $R_2$ does not denote chlorine in the para-position.

The compounds of the formula (I) can generally be prepared by a process which comprises a first stage entailing condensation and thereafter, optionally, various stages entailing substitution reactions and/or intermediate reactions, depending on the nature of the radicals $R_1$ and $R_3$ to $R_7$. The first stage consists of reacting, in accordance with the method described by J. Schmitt, C. Perrin, M. Langlois and M. Suquet (Bull. Soc. Chim. France 1963, p. 1,228), an aniline which is unsubstituted in one of the ortho-positions, whilst the other positions can respectively carry the radicals $R_4$, $R_5$, $R_6$ and $R_7$, with a phenacyl halide which can carry the $R_2$ radical, in accordance with the equation:

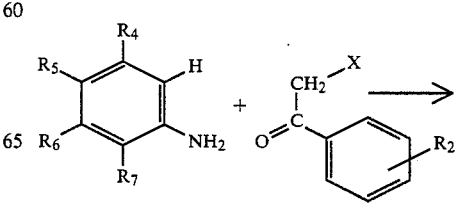

-continued

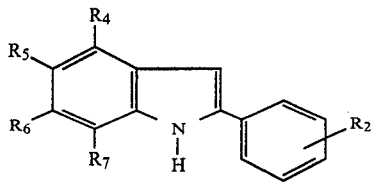

+HX
+H₂O

The reaction is carried out hot, in the presence of a solvent such as a dialkylaniline. The compounds for which $R_1$ and $R_3$ are H and which correspond to the above general formula (Ia) are thus obtained.

The other compounds of the formula (I) can thereafter be prepared in the second stage mentioned above.

The compounds for which $R_3 = H$ and $R_1$ is alkyl containing 1 to 12 carbon atoms can be obtained by a conventional alkylation process at the nitrogen atom, for example by reacting a compound of the formula (Ia) with an alkyl halide in the presence of sodium hydride in an anhydrous solvent such as dimethylformamide; these compounds correspond to the following general formula (Ib):

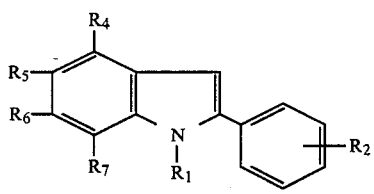

(Ib)

The preparation of the compounds of the formula (I) in which the radicals $R_1$, $R_3$, $R_4$, $R_5$, $R_6$ and $R_7$ denote H and $R_2$ denotes at least one alkyl radical containing 1 to 4 C can be carried out by reacting the corresponding alkylacetophenone, carrying the $R_2$ radical or radicals, with phenylhydrazine in the presence of polyphosphoric acid, the reaction being exothermic.

The compounds for which $R_3$ is $-S-R_8$ (and which have the formula (II)):

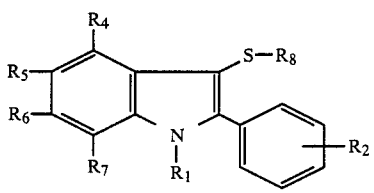

(II)

can be prepared from the compounds of the formula (Ia) via the corresponding 3-mercapto-2-phenyl-indole, the desired substitution at the sulphur atom of the mercapto group being carried out subsequently.

The 3-mercapto-2-phenyl-indole which carries the optional sustituents $R_1$, $R_2$ and $R_4$ to $R_7$ and has the formula (III) can be obtained from the corresponding compound of the formula (Ia) or (Ib) in accordance with the method described by J. Bourdais and A. Lorre (Eur. J. Med. Chem.—Chimica Therapeutica, May-June 1974, 9, No. 3, page 269), in accordance with the following equation:

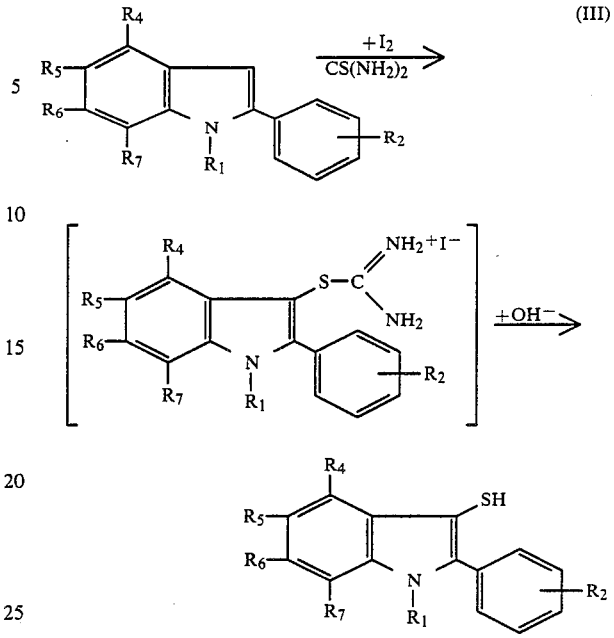

According to the abovementioned equation, a 2-phenyl-indole carrying the appropriate substituents $R_1$, $R_2$ and $R_4$ to $R_7$ is first reacted with thiourea in the presence of an alkali metal iodide in a mixture of water and an alkanol, at a low temperature, and after evaporating the mixture to dryness and washing the residue, the latter is treated with a hot solution of an alkali metal base. In the text which follows, the radical of 2-phenyl-indole will be denoted by [Y], namely:

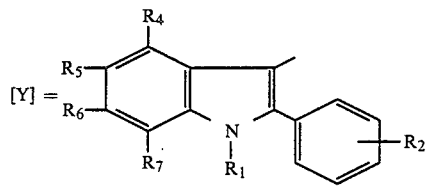

The compounds of the formula (II) in which $R_8$ is alkyl can be prepared by a conventional alkylation process, by reacting a compound of the formula (III) at elevated temperature with an alkyl halide containing 1 to 12 carbon atoms in the presence of a sodium alkylate in a solvent such as a lower alkanol containing 1 to 4 carbon atoms; the compounds obtained have the formula (IIa), namely:

$$[Y]-S-R_8 \quad (IIa)$$

The compounds of the general formula (II) which contain the $-S-R_8$ group, in which $R_8$ denotes the

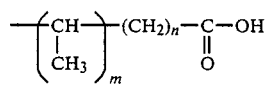

group can be prepared by reacting the mercapto radical of the corresponding compounds of the formula (III) with a halogenocarboxylic acid of the formula:

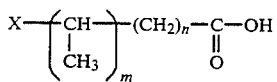

in which X denotes a halogen atom. The reaction is carried out at elevated temperature in the presence of alcoholic potassium hydroxide solution and the compounds of the formula (IIb), namely:

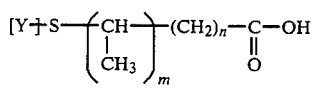

are thus obtained.

The compounds of the formula (II) which contain the —S—$R_8$ group, in which $R_8$ denotes the group of the formula:

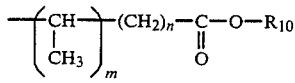

in which $R_{10}$ has the abovementioned value, can be prepared by alkylation, either by reacting a corresponding compound of the formula (III) with a corresponding halogeno-ester, or by esterification of a compound of the formula (IIb). The reaction is carried out at elevated temperature in the presence of an alkanol, and the compounds of the formula (IIc), namely:

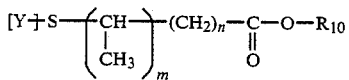

are thus obtained.

The compounds of the formula (II) containing the —S—$R_8$ group, in which $R_8$ denotes the group:

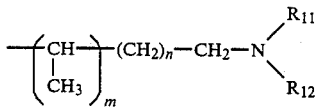

can be prepared by reacting a corresponding compound of the formula (III) with a compound of the formula:

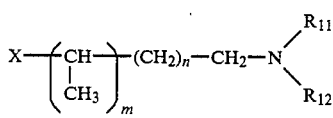

in which X denotes a halogen atom and $R_{11}$ and $R_{12}$ have the abovementioned values. The reaction is carried out at elevated temperature in an anhydrous alkanol in the presence of a sodium alkanolate in an inert atmosphere, with continuous stirring. The compounds of the formula (IId), namely:

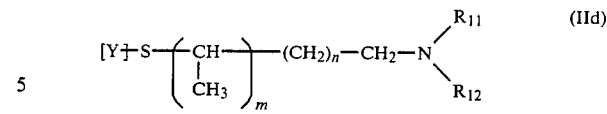

are thus obtained.

The compounds of the formula (II) which contain the —S—$R_8$ group, in which $R_8$ denotes the group:

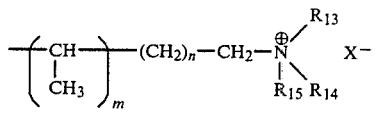

can be prepared by reacting a corresponding compound of the formula (IId), in which $R_{11}$ and $R_{12}$ are not H, with a quaternising agent X—$R_{15}$, such as an alkyl sulphate, preferably in a chlorinated solvent such as dichloroethane. The reaction takes place at ambient temperature and the compounds of the formula (IIe), namely:

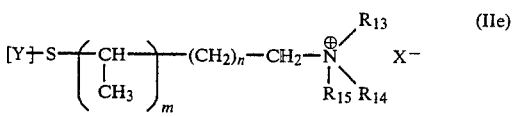

wherein $R_{13}$, $R_{14}$ and $R_{15}$ have the values already mentioned and X denotes an anion, are thus obtained.

The Examples which follow, in which the temperatures are indicated in degrees Centigrade, further illustrate the present invention. invention.

PREPARATION OF THE COMPOUNDS OF THE FORMULA Ia AND OF THE FORMULA Ib

Example 18

Preparation of 6,7-dimethyl-2-phenyl-indole having the formula Ia, in which $R_2=R_4=R_5=H$, $R_6=R_7=CH_3$. A solution of 2,3-dimethylaniline in 40 cm³ of N,N-dimethylaniline is heated at 170°. A solution containing 19.9 g of phenacyl bromide in 20 cm³ of xylene is added slowly. After all has been introduced, the reaction mixture is kept at the reflux temperature for 1 hour and the xylene as well as the water formed is then driven off under reduced pressure. The residue is taken up in a sufficient amount of hydrochloric acid and ice to dissolve the N,N-dimethylaniline. The crystals formed are filtered off, washed copiously with water, dried and recrystallised from ethanol. Melting point=134.

Example 22

Preparation of 1-butyl-2-phenyl-indole having the formula Ib, in which $R_1=C_4H_9$, $R_2=R_4=R_5=R_6=R_7=H$.

5.2 g of a suspension of sodium hydride in oil, containing 55% of the former, are added at 0° to 80 cm³ of anhydrous dimethylformamide. A solution containing 20 g of 2-phenyl-indole in 80 cm³ of anhydrous dimethylformamide is then added whilst keeping the temperature at between 0° and +5°. The temperature is allowed to rise again and the reaction mixture is left for 5 hours at 20°. It is then again cooled to 0° and 11.2 cm³ of butyl bromide are added, with constant stirring. At the end of the reaction, the mixture is slowly diluted with water and then extracted with ether. The extracts are dried and after concentration an oil distilling at 155°–157° under a pressure of 0.5 mm of mercury is obtained.

Example 38

Preparation of 2-[(2',4'-dimethyl)phenyl]-indole, of the formula:

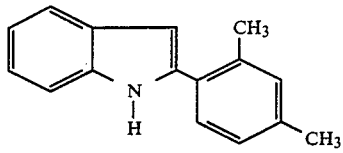

150 g of polyphosphoric acid followed by 48.5 g (0.32 mol) of 2,4-dimethyl-acetophenone and 35.4 g (0.32 mol) of phenylhydrazine are introduced into a 500 ml reactor.

The reaction is exothermic and the temperature rises to 80°–85°.

The mixture is heated to 150° and is left at this temperature, whilst stirring, for 10 minutes, after which it is allowed to cool to 110° and is slowly poured into 700 cc of hot water.

A precipitate forms, which is filtered off and washed with water.

After recrystallisation from absolute alcohol, a product which melts at 130° is obtained.

| ANALYSIS: $C_{16}H_{15}N_1$ | | | |
|---|---|---|---|
| | C | H | N |
| Theory % | 86.8 | 6.8 | 6.40 |
| Found % | 86.49 | 6.68 | 6.43 |

Example 36

Preparation of 3-(2-phenyl-indolyl)-propionic acid 29.2 g of 3-chloroethyl-2-phenyl-indole, 115 ml of DMF and 11.5 g of potassium cyanide dissolved in the minimum amount of water are heated at 70° C. for 24 hours. The whole is diluted with water and extracted with benzene. The benzene phase is washed with water, dried and concentrated in vacuo.

An oil, which crystallises in the cold and has a melting point of 112° C. is obtained. This product and 300 ml of hydrochloric acid are heated under reflux for 4 hours and the whole is then poured onto ice and filtered. The precipitate is dissolved in a hot sodium bicarbonate solution and the solution obtained is extracted with chloroform until the extracts are colourless. The aqueous phase is acidified and filtered. The product obtained is recrystallised from ethanol and then from benzene.

| Analysis: $C_{17}H_{15}NO_2$ | | | |
|---|---|---|---|
| | C | H | N |
| Theory % | 77.1 | 5.66 | 5.28 |
| Found % | 77.31 | 5.86 | 5.29 |

Example 42

Preparation of 5-(2-phenyl-indolyl)-acetic acid 10.6 g of p-aminophenyl-acetonitrile and 10.7 ml of N,N-dimethylaniline are heated at 170° C. and 5.34 g of phenacyl bromide dissolved in 6 ml of xylene are then added. The mixture is heated for one hour. The solvent is concentrated in vacuo and the residue is poured into a mixture of ice and hydrochloric acid. The whole is extracted with chloroform. The organic phase is dried and then concentrated in vacuo. The residue is recrystallised from ethanol. The product obtained is heated under reflux for one hour in a mixture consisting of 10 ml of concentrated sulphuric acid, 10 ml of acetic acid and 10 ml of water. The whole is poured onto ice and filtered. The precipitate is dissolved in a hot sodium bicarbonate solution, which is filtered and acidified. The fresh precipitate obtained is filtered off and recrystallised from ethanol.

| Analysis: $C_{16}H_{13}NO_2.\frac{1}{4}EtOH$ | | | |
|---|---|---|---|
| | C | H | N |
| Theory % | 74.45 | 5.82 | 5.10 |
| Found % | 74.77 | 5.78 | 5.16 |

Example 43

Preparation of N-(2-phenyl-indolyl)-acetic acid 5.2 g of 55% strength sodium hydride are added to 80 ml of dimethylformamide (DMF) at 0° C. under a nitrogen atmosphere. 20 g of 2-phenyl-indole dissolved in 80 ml of DMF are then added, and after the end of the addition the whole is left to stand for 5 hours at 20° C. 20 g of ethyl bromoacetate dissolved in 20 ml of DMF are added to the cooled mixture and the whole is left to stand overnight. The DMF is then distilled and the residue is taken up in water. The aqueous phase is extracted with ethyl acetate. The organic phase is dried and concentrated in vacuo. 20 g of an oily product are recovered. This crude oil is treated with 19 g of KOH in 500 ml of methanol under reflux for one hour. It is concentrated to dryness, the residue is taken up in hot water and the solution is filtered. The filtrate is acidified; a black gum is formed, which is filtered off and recrystallised twice from ethanol and once from benzene.

| Analysis: $C_{16}H_{13}NO_2$ | | | |
|---|---|---|---|
| | C | H | N |
| Theory % | 76.6 | 5.18 | 5.59 |
| Found % | 76.71 | 5.38 | 5.8 |

Example 44

Preparation of 3-(2-phenyl-indolyl)-acetic acid 167.5 ml of 40% strength dimethylamine followed by 45 ml of 40% strength formaldehyde are added to 450 ml of acetic acid cooled to 10° C. The solution thus obtained is then poured onto 45 g of 2-phenyl-indole. The mixture is left for 8 hours at ambient temperature and then filtered and rendered alkaline with a potassium hydroxide solution. Thereafter it is extracted with ether. The organic phase is dried and concentrated in vacuo. The residue is dissolved in a mixture containing 300 ml of ethanol and 150 ml of ether, to which 30 ml of methyl iodide are added. The whole is left to stand overnight and after adding isopropyl ether an oil is obtained, which is recovered.

This oil is dissolved in 350 ml of DMF and 36.4 g of sodium cyanide are added. The mixture is heated under reflux for 20 hours. The whole is poured into water and extracted with ethyl acetate. After drying and concentrating the organic phase, a heavy oil is recovered.

This table includes the compounds 36, 37 and 45, in which $R_3$ is different from H.

TABLE II

| Example No. | $R_1$ | $R_2$ | $R_3$ | $R_4$ | $R_5$ | $R_6$ | $R_7$ | Melting point |
|---|---|---|---|---|---|---|---|---|
| 1 | H | H | | H | $CH_3$ | H | $CH_3$ | 86° |
|  | H | 4'-Cl | | H | $OCH_3$ | H | H | 180° |
| 2 | H | H | | $CH_3$ | H | H | $CH_3$ | 72° |
| 25 | H | 4'$OCH_3$ | | H | H | H | H | 230° |
| 29 | H | H | | H | $CH_3$ | $CH_3$ | H | 230° |
| 26 | H | H | | $CH_3$ | $CH_3$ | H | H | 137° |
| 3 | H | H | | $CH_3$ | H | $CH_3$ | H | 105° |
| 28 | $C_{12}H_{25}$ | H | | H | H | H | H | oil which cannot be distilled |
| 18 | H | H | | H | H | $CH_3$ | $CH_3$ | 134° |
| 22 | $C_4H_9$ | H | | H | H | H | H | oil* |
| 34 | H | H | | H | $-OCH_3$ | $-OCH_3$ | H | 185° |
| 38 | H | 2'-$CH_3$; 4'-$CH_3$ | | H | H | H | H | 130° |
| 41 | H | 2'-$CH_3$; 4'-$CH_3$ | | H | H | $CH_3$ | $CH_3$ | 102° |
| 44 | $OH_2-COOH$ | H | H | H | H | H | H | 181° |
| 33 | CH—COOH \| $CH_3$ | H | H | H | H | H | H | 250° |
| 43 | H | H | H | H | $-CH_2-COOH$ | H | H | 217° |
| 45 | H | H | $CH_2-COOH$ | H | H | H | H | 174° |
| 36 | H | H | $((CH_2)_2-COOH)$ | H | H | H | H | 154° |
| 37 | H | H | $CH_2-COOH$ | $CH_3$ | H | H | $CH_3$ | 210° |

*(boiling point under 0.5 mm Hg = 155–157° C.)

A mixture consisting of the above oil, 159 ml of methylcellosolve and 63.5 g of potassium hydroxide is heated under reflux for 20 hours, washed with water and filtered. The filtrate is acidified and the precipitate obtained is extracted repeatedly with hot benzene and recrystallised from benzene.

| Analysis: $C_{16}H_{15}NO_2$ | | | |
|---|---|---|---|
|  | C | H | N |
| Theory % | 76.5 | 5.18 | 5.58 |
| Found % | 76.35 | 5.2 | 5.76 |

The hydrazone obtained, and 68 g of polyphosphoric acid, are heated to 90° C. The temperature thereafter rises rapidly to 130° C. The mixture is cooled and the whole is poured into a mixture of water and ice. The resulting mixture is heated at 50° C. to hydrolyse the polyphosphoric acid and the whole is then filtered.

The ester obtained is hydrolysed for 16 hours by means of 175 ml of sulphuric acid which has been diluted two-fold. The whole is poured into water and the precipitate is filtered off and recrystallised from isopropanol.

| Analysis: $C_{16}H_{13}NO_2$ | | | |
|---|---|---|---|
|  | C | H | N |
| Theory % | 76.5 | 5.18 | 5.58 |
| Found % | 76.36 | 5.24 | 5.47 |

Tables II which follow show the compounds of the formula Ia and Ib which have been prepared analogously to the process of Examples 18 and 22.

This table indicates the meaning of the radicals $R_1$, $R_2$ and $R_4$ to $R_7$ as well as the melting point of the compounds obtained. It contains the compounds 1, 2, 3, 18, 22, 25, 26, 28, 29, 33, 34, 36, 37, 38, 41 and 43, the (ultraviolet) filtration properties of which are indicated in Table I.

PREPARATION OF THE COMPOUNDS OF THE FORMULA IIa, IIb, IIc, IId AND IIe

Example 7

Preparation of 3-dodecylmercapto-2-phenyl-indole having the formula IIa, in which $R_8=C_{12}H_{25}$ and $R_1=R_2=R_4=R_5=R_6=R_7=H$. A solution containing 30 g of 3-mercapto-2-phenyl-indole in 100 cm³ of methanol is added, under a nitrogen atmosphere and with constant stirring, to a solution of sodium methylate obtained from 3.06 g of sodium and 200 cm³ of methanol. Thereafter 30 g of dodecyl bromide are introduced slowly and the mixture is heated under reflux for 3 hours. It is concentrated to dryness, the residue is taken up with water and the whole is extracted with ethyl acetate. The organic extracts are washed with 10% strength sodium hydroxide solution and then with water, and are finally dried. When concentrated, they give an oil which cannot be distilled and which is purified by chromatography on silica gel, using an 85:15 mixture of cyclohexane and ethyl acetate as the eluant.

| Analysis: $C_{26}H_{35}NS$ | | | |
|---|---|---|---|
|  | C | H | N |
| Theory % | 79.4 | 8.92 | 3.56 |
| Found % | 79.13 | 8.50 | 3.55 |

Example 14

Preparation of (4,7-dimethyl-2-phenyl-indolyl-3)-thioacetic acid having the formula IIb, in which m=0, n=1, $R_1=R_2=R_5=R_6=H$ and $R_4=R_7=CH_3$.

Stage (1):

4.92 g of thiourea and a solution containing 16.4 g of iodine and 16.2 g of potassium iodide in 35 cm³ of water are added successively, under a nitrogen atmosphere, to a solution containing 14.3 g of 4,7-dimethyl-2-phenyl-indole in 160 cm³ of methanol containing 10% of water. The whole is stirred for 2½ hours whilst maintaining the temperature at between 30° and 35°. It is then evaporated to dryness and the residue is washed with ether. This residue is then treated with 162 cm³ of normal sodium hydroxide solution for 30 minutes at 90°. After cooling, the whole is acidified with acetic acid and extracted with chloroform. After having dried the extracts, they are concentrated to dryness and 12 g of 4,7-dimethyl-3-mercapto-2-phenyl-indole are obtained.

Stage (2):

11.3 g of the compound obtained in (1) are dissolved in 94 cm³ of normal alcoholic potassium hydroxide solution under a nitrogen atmosphere, 4.65 g of chloroacetic acid are added and the mixture is heated for 3 hours at 70° whilst stirring. It is then concentrated to dryness, the residue is taken up in water, the insoluble matter is filtered off and the filtrate is acidified with 20% strength hydrochloric acid to pH 4. The whole is extracted with ethyl acetate and the extract is dried and concentrated under reduced pressure to give an oil which crystallises on addition of isopropyl ether. Melting point 136°.

| Analysis: $C_{18}H_{17}NO_2S$ | | | |
|---|---|---|---|
| | C | H | N |
| Theory % | 69.4 | 5.7 | 4.5 |
| Found % | 69.37 | 5.82 | 4.35 |

Example 12

Preparation of ethyl (5-methyl-2-phenyl-indolyl-3)-thioacetate having the formula IIc, in which $m=0$, $n=1$, $R_1=R_2=R_4=R_6=R_7=H$, $R_5=CH_3$ and $R_{10}=C_2H_5$.

11.95 g of 5-methyl-3-mercapto-2-phenyl-indole are dissolved in 100 cm³ of methanol under a nitrogen atmosphere and 8.35 g of ethyl bromoacetate and 5.6 g of triethylamine are then added. The temperature rises to 50°–60°. This temperature is maintained for 3 hours and the mixture is then concentrated to dryness. The residue is dissolved in ethyl acetate and the solution is washed with dilute hydrochloric acid, then with a sodium bicarbonate solution and finally with water. After having dried and concentrated the extracts, a residue is obtained, which crystallises from isopropanol. Melting point = 90°

| Analysis: $C_{19}H_{19}NO_2S$ | | | |
|---|---|---|---|
| | C | H | N |
| Theory % | 65.3 | 4.8 | 4.48 |
| Found % | 65.15 | 5.02 | 4.43 |

Example 8

Preparation of 3-(3-dimethylamino-propylthio)-2-phenyl-indole having the formula IId, in which $m=0$, $n=2$, $R_1=R_2=R_4=R_5=R_6=R_7=H$ and $R_{11}=R_{12}=CH_3$.

A solution of sodium ethylate obtained from 0.675 g of sodium and 50 cm³ of ethanol, followed by 2.32 g of 3-chloro-N,N-dimethylpropylamine hydrochloride, are added to a solution containing 3.3 g of 3-mercapto-2-phenyl-indole in 10 cm³ of anhydrous ethanol under a nitrogen atmosphere, with constant stirring. Stirring is continued for 2 hours at ordinary temperature and the mixture is then concentrated to dryness. The residue is taken up in water and the mixture obtained is extracted with ether. After having dried and evaporated the solvent, a residue is obtained, which crystallises from ethanol. Melting point 140°.

| Analysis: $C_{19}H_{22}N_2S$ | | | |
|---|---|---|---|
| | C | H | N |
| Theory % | 73.7 | 7.12 | 9.04 |
| Found % | 73.64 | 7.40 | 8.82 |

Example 9

Preparation of 3-(2-phenyl-indolyl-3-thio)-propyl-trimethylammonium methosulphate having the formula IIe, in which $m=0$, $n=2$, $R_1=R_2=R_4=R_5=R_6=R_7=H, R_{13}=R_{14}=R_{15}=CH_3$ and $X=CH_3SO_4^\ominus$.

5 g of 3-(3-dimethylamino-propylthio)-2-phenyl-indole are dissolved in 60 cm³ of dichloroethane. 2.24 g of dimethyl sulphate are added. The whole is stirred for 1 hour at ambient temperature and the reaction product is precipitated by adding isopropyl ether. After recrystallisation from ethanol, the expected compound is obtained. Melting point 95°.

Table III which follows indicates the compounds of the formulae (IIa) to (IIe) which have been prepared analogously to the processes of Examples 7, 14, 12, 8 and 9.

This table gives the values of the radicals $R_1$, $R_2$ and $R_4$ to $R_9$ as well as that of the parameters m and n and the melting point of the compounds obtained.

It includes compounds 4 to 17, for which the (ultraviolet) filtration properties have already been indicated in Table I.

TABLE III

| Example No. | $R_1$ | $R_2$ | $R_4$ | $R_5$ | $R_6$ | $R_7$ | $R_8$ | $R_9$ | m | n | Melting point |
|---|---|---|---|---|---|---|---|---|---|---|---|
| | H | H | H | H | H | H | $C_4H_9$ | — | — | | oil |
| | H | H | H | H | H | H | $C_8H_{17}$ | — | — | | oil |
| 4 | H | H | H | H | H | H | " | COOH | 0 | 1 | 144 |
| 6 | H | H | H | $OCH_3$ | H | H | " | COOH | 0 | 1 | 200 |
| 16 | H | H | H | $CH_3$ | H | H | " | COOH | 0 | 1 | 164 |
| 5 | H | 4'-Cl | H | $OCH_3$ | H | H | " | COOH | 0 | 1 | 204 |
| 13 | $CH_3$ | H | H | H | H | H | " | COOH | 0 | 1 | 160 |
| 15 | H | H | H | H | $CH_3$ | $CH_3$ | " | COOH | 0 | 1 | 170 |
| 17 | H | H | H | $CH_3$ | H | $CH_3$ | " | COOH | 0 | 1 | 145 |
| 11 | H | H | H | H | H | H | " | $COOC_2H_5$ | 0 | 1 | 88 |

TABLE III-continued

| Example No. | $R_1$ | $R_2$ | $R_4$ | $R_5$ | $R_6$ | $R_7$ | $R_8$ | $R_9$ | m | n | Melting point |
|---|---|---|---|---|---|---|---|---|---|---|---|
| 10 | H | H | H | H | H | H | " | $CH_2N\begin{smallmatrix}CH_3\\CH_3\end{smallmatrix}$ | 0 | 1 | 208 |
|  | H | H | H | H | H | H | " | $CH_2NH_2$ | 0 | 1 | 121 |
|  | H | H | H | H | H | H | " | COOH | 1 | 0 | 155 |
| 7 | H | H | H | H | H | H | $C_{12}H_{25}$ | — |  |  | oil |
| 8 | H | H | H | H | H | H | " | $CH_2N\begin{smallmatrix}CH_3\\CH_3\end{smallmatrix}$ | 0 | 2 | 140 |
| *9 | H | H | H | H | H | H | " | $CH_2\overset{+}{N}\begin{smallmatrix}CH_3\\CH_3\\|\\CH_3\end{smallmatrix}$ | 0 | 2 | 95 |
| 12 | H | H | H | $CH_3$ | H | H | $C_{12}H_{25}$ | $COOC_2H_5$ | 0 | 1 | 90 |
| 14 | H | H | $CH_3$ | H | H | $CH_3$ | " | COOH | 0 | 1 | 136 |
| 30 | H | H | H | $CH_3$ | H | $CH_3$ | " | COOH | 1 | 0 | 171 |
| 31 | H | H | H | $OCH_3$ | H | H | " | $CH_2N\begin{smallmatrix}H\\C_4H_9\end{smallmatrix}$ | 0 | 1 | 135 |
| *32 | H | H | H | H | H | H | " | $CH_2-\overset{+}{N}-(CH_3)_3$ | 0 | 2 | 111 |
| 35 | H | H | H | $-OCH_3$ | $-OCH_3$ | H | " | COOH | 0 | 1 | 204° |
| 40 | H | $2'-CH_3;4'-CH_3$ | H | H | H | H | " | $(-CH_2-N(CH_3)_2)$ | 0 | 2 | 163° |
| 39 | H | $2'-CH_3;4'-CH_3$ | H | H | H | H | " | COOH | 0 | 1 | 140° |

*Compound 9 is a methosulphate and 32 is an iodide

FORMULATION EXAMPLES

A. The following anti-sunburn oils, containing the constituents shown, are prepared:

| Oil $A_1$: | |
|---|---|
| Compound of Example 1 | 2 g |
| Cacao butter | 2.5 g |
| Butylhydroxyanisole | 0.05 g |
| Perfume | 0.5 g |
| Vegetable oil, q.s.p | 100 g |
| Oil $A_2$: | |
| Compound of Example 11 | 2 g |
| Lanoline | 2.5 g |
| Butylhydroxyanisole | 0.05 g |
| Perfume | 0.5 g |
| Triglycerides of fatty acids ($C_8$ to $C_{12}$), q.s.p | 100 g |
| Oil $A_3$: | |
| Compound of Example 41 | 3 g |
| Cacao butter | 2.5 g |
| Butylhydroxyanisole antioxidant | 0.05 g |
| Perfume | 0.5 g |
| Vegetable oil, q.s.p | 100 g |

B. The following oil/alcohol anti-sunburn lotion, containing the constituents shown, is prepared:

| Lotion $B_1$: | |
|---|---|
| Compound of Example 3 | 5 g |
| Lanoline | 2.45 g |
| Butylhydroxytoluene | 0.05 g |
| Perfume | 0.5 g |
| Triglycerides of fatty acids ($C_8$ to $C_{12}$) | 46 g |
| Alcohol, 96° strength | 46 g |
| Lotion $B_2$: | |
| Compound of Example 36 | 5 g |
| Triglycerides of fatty acids ($C_8$ to $C_{12}$) | 47.5 g |
| Ethanol, 96° strength | 47 g |
| Perfume | 0.5 g |
| Lotion $B_3$: | |
| Compound of Example 37 | 5 g |
| Lanoline | 2.45 g |
| Butylhydroxytoluene | 0.05 g |
| Perfume | 0.50 g |
| Triglycerides of fatty acids ($C_8$ to $C_{12}$) | 46 g |
| Ethanol, 96° strength | 46 g |
| Lotion $B_4$: | |
| Compound of Example 40 | 2 g |
| Triglycerides of fatty acids ($C_8$ to $C_{12}$) | 47.5 g |
| Ethanol, 96° strength | 47 g |
| Perfume | 0.5 g |

C. The following anti-sunburn foam, containing the constituents shown, is prepared:

| Foam $C_1$: | |
|---|---|
| Triglycerides of fatty acids ($C_8$ to $C_{12}$) | 50 g |
| Stearic acid | 1 g |
| Oleyl alcohol | 2 g |
| Triethanolamine | 1 g |
| Acrylic polymer | 0.5 g |
| Compound of Example 13 | 3 g |
| Triethanolamine para-hydroxybenzoate | 0.3 g |
| Perfume | 0.5 g |
| Water, q.s.p | 100 g |
| Active constituents, of the above formulation | 87% |
| Freon 12 ($CCl_2F_2$) | 13% |
| Foam $C_2$: | |
| Triglycerides of fatty acids ($C_8$ to $C_{12}$) | 50 g |
| Stearic acid | 1 g |
| Triethanolamine | 1 g |
| Oleyl alcohol | 2 g |
| Acrylic polymer thickener | 0.5 g |

| | |
|---|---|
| Compound of Example 41 | 3 g |
| Para-hydroxybenzoate | 0.3 g |
| Perfume | 0.5 g |
| Demineralised water, q.s.p | 100 g |
| Active composition, as above: | 87% |
| Freon 12: | 13% |

D. The following anti-sunburn creams, containing the constituents shown, are prepared:

| | |
|---|---|
| Cream $D_1$: | |
| Triglycerides of fatty acids ($C_8$ to $C_{12}$) | 30 g |
| Glycerol monostearate | 6 g |
| Stearic acid | 2 g |
| Cetyl alcohol | 1.2 g |
| Lanoline | 4 g |
| Methyl para-hydroxybenzoate | 0.3 g |
| Propylene glycol | 2 g |
| Triethanolamine | 0.5 g |
| Compound of Example 2 | 3 g |
| Perfume | 0.5 g |
| Water, q.s.p | 100 g |
| Cream $D_2$: | |
| $C_{16}$-$C_{18}$ fatty alcohols polyoxyethyleneated with 15 mols of ethylene oxide | 9 g |
| Triglycerides of fatty acids ($C_8$ to $C_{12}$) | 26 g |
| Isopropyl myristate | 4 g |
| Silicone oil | 2 g |
| Cetyl alcohol | 1.5 g |
| Compound of Example 1 | 2 g |
| Glycerol | 10 g |
| Propyl para-hydroxybenzoate | 0.3 g |
| Perfume | 0.3 g |
| Water, q.s.p | 100 g |
| Cream $D_3$: | |
| Triglycerides of fatty acids ($C_8$ to $C_{12}$) | 30 g |
| Glycerol monostearate | 6 g |
| Stearic acid | 2 g |
| Cetyl alcohol | 1.2 g |
| Lanoline | 4 g |
| Para-hydroxybenzoate | 0.3 g |
| Propanediol | 2 g |
| Triethanolamine | 0.5 g |
| Compound of Example 36 | 1.5 g |
| Perfume | 0.5 g |
| Demineralised water, q.s.p | 100 g |
| Cream $D_4$: | |
| Fatty alcohols ($C_{16}$-$C_{18}$) polyoxyethyleneated with 15 mols of ethylene oxide | 9 g |
| Triglycerides of fatty acids ($C_8$ to $C_{12}$) | 26 g |
| Isopropyl myristate | 4 g |
| Dimethylpolysiloxane | 2 g |
| Cetyl alcohol | 1.5 g |
| Compound of Example 39 | 2.5 g |
| Propanetriol | 10 g |
| Para-hydroxybenzoate | 0.3 g |
| Perfume | 0.3 g |
| Demineralised water, q.s.p | 100 g |

E. The following anti-sunburn milk, containing the constituents shown, is prepared:

| | |
|---|---|
| Milk $E_1$: | |
| Cetyl/stearyl alcohol oxyethyleneated with 15 mols of ethylene oxide | 2 g |
| Cetyl alcohol | 2 g |
| Triglycerides of fatty acids ($C_8$ to $C_{12}$) | 20 g |
| Lanoline | 4 g |
| Stearic acid | 0.5 g |
| Silicone oil | 0.3 g |
| Nipaester 82-121 (a mixture of methyl, ethyl, butyl and benzyl para-hydroxybenzoates) | 0.3 g |
| Acrylic polymer | 0.15 g |
| Triethanolamine | 0.2 g |
| Compound of Example 3 | 2 g |
| Perfume | 0.4 g |
| Water, q.s.p | 100 g |
| Milk $E_2$: | |
| Cetyl stearyl alcohol containing 15 mols of ethylene oxide (EO) | 2 g |
| Cetyl alcohol | 2 g |
| Triglycerides of fatty acids ($C_8$ to $C_{12}$) | 20 g |
| Lanoline | 4 g |
| Stearic acid | 0.5 g |
| Dimethylpolysiloxane | 0.3 g |
| Para-hydroxybenzoate | 0.3 g |
| Acrylic polymer thickener | 0.15 g |
| Triethanolamine | 0.20 g |
| Compound of Example 39 | 2 g |
| Perfume | 0.40 g |
| Demineralised water, q.s.p | 100 g |

F. The following aqueous-alcoholic anti-sunburn gel, containing the constituents shown, is prepared:

| | |
|---|---|
| Gel $F_1$: | |
| Acrylic polymer | 0.7 g |
| Triethanolamine | 0.35 g |
| Propylene glycol | 25 g |
| Alcohol, 96° strength | 25 g |
| Compound of Example 18 | 1.5 g |
| Nipaester 82-121 (a mixture of methyl, ethyl, butyl and benzyl para-hydroxybenzoates) | 0.3 g |
| Perfume | 0.3 g |
| Water, q.s.p | 100 g |
| Gel $F_2$: | |
| Compound of Example 36 | 2.5 g |
| Acrylic polymer thickener | 0.7 g |
| Triethanolamine | 0.35 g |
| Propanediol | 25 g |
| Ethanol, 96° strength | 25 g |
| Para-hydroxybenzoate | 0.3 g |
| Perfume | 0.3 g |
| Demineralised water, q.s.p | 100 g |
| Gel $F_3$: | |
| Acrylic polymer thickener | 0.7 g |
| Triethanolamine | 0.35 g |
| Propylene glycol | 25 g |
| Ethanol, 96° strength | 25 g |
| Compound of Example 37 | 1.5 g |
| Para-hydroxybenzoate | 0.3 g |
| Perfume | 0.3 g |
| Demineralised water, q.s.p | 100 g |
| Gel $F_4$: | |
| This has the formulation of the preceding alcohol-based anti-sunburn gel, with 1% of the compound of Example 42, instead of the compound of the example 37. | |
| Jelly $F_5$: | |
| This has the same formulation as in the case of $F_3$, but replacing 1.50 g of the compound of Example 37 by 1.25 g of the compound of Example 40. | |

G. The following anti-sunburn stick, containing the constituents shown, is prepared:

| | |
|---|---|
| Stick $G_1$: | |
| Compound of Example 7 or of Example 20 | 5 g |
| Cacao butter | 10 g |
| Ozokerite | 20 g |
| Oleyl alcohol | 6 g |
| Lanoline | 8 g |
| Propyl gallate | 0.05 g |
| Castor oil | 8 g |
| Perfume | 0.5 g |
| Triglycerides of fatty acids ($C_8$ to $C_{12}$), q.s.p | 100 g |
| Stick $G_2$: | |
| Cacao butter | 10 g |
| Ozokerite | 20 g |
| Compound of Example 41 | 5 g |
| Oleyl alcohol | 6 g |
| Lanoline | 8 g |

| -continued | |
|---|---|
| Propyl gallate | 0.05 g |

The 7 types of composition A to G above, can be prepared in particular with at least one of the compounds No. 1, 2, 3 and 18 and in the proportions indicated respectively for each type of composition, that is to say, in particular:

2% in the oil or milk (A₁, A₂ or E)
5% in the lotion (B)
3% in the foam (C)
3% or 2% in the creams (D₁ and D₂)
1.5% in the gel (F)
2% in the stick (G)

On the other hand:

The anti-sunburn lotion can also be formulated with 5% of the compound of Example 4, the anti-sunburn cream D₁ can also be formulated with 3.5% of the compound of Example 7, the anti-sunburn milk can also be formulated with 2.5% of the compound of Example 20, and the anti-sunburn gel can also be formulated with 3% of the compound of Example 17.

We claim:

1. A cosmetic composition comprising a cosmetic vehicle and at least about 0.05 percent by weight based on the total weight of said composition of a compound of the formula

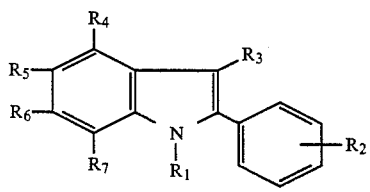

wherein $R_1$ is selected from the group consisting of hydrogen, alkyl containing 1 to about 12 carbon atoms and optionally branched carboxyalkyl radical containing 1 to 4 carbon atoms, $R_2$ is selected from the group consisting of hydrogen, alkoxy containing 1 to 4 carbon atoms, at least one alkyl and carboxyalkyl radical containing 1 to 4 carbon atoms and halogen,

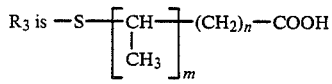

wherein m is 0 or 1 and n is 0, 1 or 2, and each of $R_4$, $R_5$, $R_6$ and $R_7$ is independently selected from the group consisting of hydrogen, alkyl containing 1–4 carbon atoms, carboxyalkyl containing 1–4 carbon atoms and alkoxy containing 1–4 carbon atoms.

2. The composition of claim 1 wherein $R_3$ represents —S—CH₂—COOH, —S—CH₂—COOC₂H₅ or

—S—CH—COOH.
    |
  CH₃

3. A cosmetic composition comprising a cosmetic vehicle and at least about 0.05 percent by weight based on the total weight of said composition of a compound of the formula

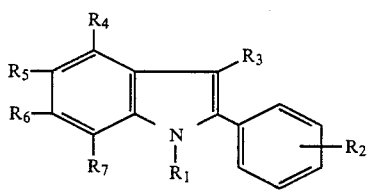

wherein $R_1$ is selected from the group consisting of hydrogen, alkyl containing 1 to about 12 carbon atoms and optionally branched carboxyalkyl radical containing 1 to 4 carbon atoms, $R_2$ is selected from the group consisting of hydrogen, alkoxy containing 1 to 4 carbon atoms, at least one alkyl and carboxyalkyl radical containing 1 to 4 carbon atoms and halogen, $R_3$ is —S(CH₂)₃N(CH₃)₂, —S(CH₂)₂N(CH₃)₂ or —S(CH₂)₂NHC₄H₉, and each of $R_4$, $R_5$, $R_6$ and $R_7$ is independently selected from the group consisting of hydrogen, alkyl containing 1–4 carbon atoms, carboxyalkyl containing 1–4 carbon atoms and alkoxy containing 1–4 carbon atoms.

4. A process for protecting a cosmetic composition liable to deteriorate in the presence of light radiation which comprises incorporating therein in an amount from about 0.05 to about 5 percent by weight based on the weight of the composition a compound of the formula

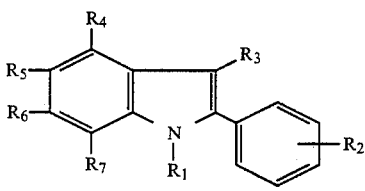

wherein $R_1$ is selected from the group consisting of hydrogen, alkyl containing 1 to about 12 carbon atoms and optionally branched carboxyalkyl radical containing 1 to 4 carbon atoms, $R_2$ is selected from the group consisting of hydrogen, alkoxy containing 1 to 4 carbon atoms, at least one alkyl and carboxyalkyl radical containing 1 to 4 carbon atoms and halogen, $R_3$ is selected from the group consisting of —SCH₂COOH, —SCH₂COOC₂H₅, —SCH(CH₃)COOH, —S(CH₂)₃N(CH₃)₂, —S(CH₂)₂N(CH₃)₂, —S(CH₂)₂NHC₄H₉, H, —CH₂CH₂COOH and —CH₂COOH, and each of $R_4$, $R_5$, $R_6$ and $R_7$ is independently selected from the group consisting of hydrogen, alkyl containing 1–4 carbon atoms, carboxyalkyl containing 1–4 carbon atoms and alkoxy containing 1–4 carbon atoms, with the proviso that when $R_3$ represents hydrogen at least one of the radicals $R_1$, $R_2$, $R_4$, $R_5$, $R_6$ and $R_7$ is not hydrogen.

* * * * *